United States Patent [19]
Kalamasz

[11] Patent Number: 5,695,989
[45] Date of Patent: Dec. 9, 1997

[54] APPARATUS AND METHOD FOR SEPARATING PARTICLES USING A PLIABLE VESSEL

[75] Inventor: Dale Kalamasz, Redmond, Wash.

[73] Assignee: CellPro, Inc., Bothell, Wash.

[21] Appl. No.: 510,896

[22] Filed: Aug. 3, 1995

Related U.S. Application Data

[63] Continuation of Ser. No. 116,899, Sep. 3, 1993, abandoned, which is a continuation of Ser. No. 957,408, Nov. 18, 1992, abandoned, which is a continuation of Ser. No. 599,796, Oct. 18, 1990, abandoned.

[51] Int. Cl.$^6$ .............................. C12M 1/00; C12M 1/02
[52] U.S. Cl. ............... 435/308.1; 210/276; 210/282; 210/670; 422/70; 422/101; 435/2; 435/239; 436/161
[58] Field of Search ............... 422/70, 101, 212, 422/215, 221, 267, 294; 435/2, 239, 308.1; 436/161; 210/661, 670, 672, 276, 282

[56] References Cited

U.S. PATENT DOCUMENTS

| | | | |
|---|---|---|---|
| 2,063,086 | 12/1936 | Fitz Gerald | 210/131 |
| 3,625,652 | 12/1971 | Fujimoto et al. | |
| 3,692,493 | 9/1972 | Terasaki | |
| 3,843,324 | 10/1974 | Edelman et al. | |
| 3,970,518 | 7/1976 | Giaever | |
| 3,986,834 | 10/1976 | Steinbrink, Jr. | |
| 4,230,635 | 10/1980 | Senyei et al. | 424/12 |
| 4,647,539 | 3/1987 | Bach | |
| 4,787,971 | 11/1988 | Donald | 210/198.2 |
| 4,839,280 | 6/1989 | Banes | |
| 4,871,463 | 10/1989 | Taylor et al. | 210/161 |
| 4,904,600 | 2/1990 | Ramp | |
| 4,931,400 | 6/1990 | Jitsukawa | |
| 5,215,926 | 6/1993 | Etchells, III et al. | 436/501 |
| 5,215,927 | 6/1993 | Berenson et al. | 436/541 |
| 5,225,353 | 7/1993 | Berenson et al. | 436/541 |
| 5,240,856 | 8/1993 | Goffe et al. | |
| 5,262,334 | 11/1993 | Berenson et al. | 436/541 |
| 5,378,624 | 1/1995 | Berenson et al. | 435/239 |
| 5,506,130 | 4/1996 | Peterson et al. | 435/240.1 |

FOREIGN PATENT DOCUMENTS

| | | |
|---|---|---|
| 60-11135 | 1/1985 | Japan. |
| WO 87/04628 | 8/1987 | WIPO. |
| WO 91/16088 | 10/1991 | WIPO. |
| WO 91/16116 | 10/1991 | WIPO. |
| WO 91/16452 | 10/1991 | WIPO. |
| WO 92/07243 | 4/1992 | WIPO. |
| WO 93/08258 | 4/1993 | WIPO. |

OTHER PUBLICATIONS

Biorad Catalog p. 56, 85–86 (1988).
Miltenyi et al., "High Gradient Magnetic Cell Separation With MACS," *Cytometry* 11:231–238, 1990.

(List continued on next page.)

*Primary Examiner*—Jill Warden
*Assistant Examiner*—Jan M. Ludlow
*Attorney, Agent, or Firm*—Seed & Berry LLP

[57] ABSTRACT

A method and apparatus for separating target particles from a mixture of target and non-target particles. The apparatus includes a vessel having an inlet through which the mixture may be introduced and an outlet through which the fluid may exit, at least a portion of which is pliable; a bed of binding material disposed within the vessel, the binding material attracting the target particles such that the target particles may become bound thereto and being porous enough to allow the non-target particles to pass therethrough; and a screen disposed below the binding material for retaining the binding material in place. The pliable portion of the vessel permits the user to separate the target particles from the binding material by merely squeezing the pliable portion in such a manner as to cause relative movement in the binding material, thereby creating the necessary degree of agitation to cause the target particles to become dislodged from the binding material. The deformation of the pliable vessel can be accomplished by either the user physically squeezing the vessel with his/her hand or using an external apparatus that applies the necessary force to the vessel.

16 Claims, 1 Drawing Sheet

OTHER PUBLICATIONS

Berenson et al., "Positive selection of viable cell populations using avidin–biotin immunoadsorption," *Journal of Immunological Methods* 91: 11–19, 1986.

Basch et al., "Cell Separation Using Positive Immunoselective Techniques," *Journal of Immunological Methods* 56: 269–280, 1983.

Fredrickson and Basch "L3T4 Antigen Expression By Heompoietic Precusor Cells," *Journal of Experimental Medicine* 169: 1473–78, 1989.

Olson et al., "Dissociation Kinetics of Antigen–Antibody Interactions: Studies on a Panel of Anti–Albumin Monoclonal Antibodies," *Molecular Immunology* 26(2): 129–136, 1989.

Thomas et al, "Specific binding and release of cells from beads using cleavable tetrameric antibody complexes," *Journal Immunological Methods* 120(2): 221–231, 1989.

Wilchek and Bayer, "The Avidin–Biotin Complex in Bioanalytical Applications," *Analytical Biochemistry* 171:1–32, 1988.

Civin and Loken, "Cell Surface Antigens of Human Marrow Cells: Dissection of Hematopoietic Development Using Monoclonal Antibodies and Multiparameter Flow Cytometry," *International Journal of Cell Cloning* 5: 267–288, 1987.

Suzuki and Dale, "Biotinylated Erythrocytes: In Vivo Survial and In Vitro Recovery," *Blood* 70(3): 791–795, 1987.

Updyke and Nicolson, "Immunoaffinity Isolation of Membrane Antigens with Biotinylated Monoclonal Antibodies and Streptavidin—Agarose," *Methods in Enzymology* 121: 717–725, 1986.

Fuccillo, "Application of the Avidin–Biotin Technique in Microbiology," *BioTechniques* 3(6):494–501, 1985.

Wormmeester et al., "A Simple Method for Immunoselective Cell Separation with the Avidin–Biotin System," *Journal of Immunological Methods* 67: 389–394, 1984.

Kumar and Lykke, "Cell Separation: A Review," *Pathology* 16:53–62, 1984.

Bonnafous et al., "Cell Affinity Chromatography with Ligands Immobilized through Cleavable Mercury—Sulfur Bonds," *Journal of Immunological Methods* 58: 93–107, 1983.

Fong, "Solid–Phase Fractionation of Lymphoid Cells on Ligand–Coated Plastic Plates," *Cell Separation: Methods and Selected Applications* 2:203–219, 1983.

Lakow and Basch, "Positive Immunoselection Using Antibody–Enzyme Complexes," *Journal of Immunological Methods* 44: 135–151, 1981.

Wysocki and Sato, "Panning for lymphocytes: A method for cell selection," *Proc. Natl. Acad. Sci. USA* 75: 2844–2848, 1978.

Ghetie et al., "Separation of Cells by Affinity Chromatography on SpA–Sephrose 6MB," *Journal of Immunological Methods* 21: 133–141, 1978.

Wigzell, "Specific Affinity Fractionation of Lymphocytes Using Glass or Plastic Bead Columns," *Scandinavian Journal of Immunology* 5(Suppl. 5): 23–30, 1976.

Jasiewicz et al., "Selective Retieval of Biotin–Labeled Cells using Immobilized Avidin," *Experimental Cell Research* 100: 213–217, 1976.

Kiefer et al., "Separation of antigen–specific lymphocytes: A new general method of releasing cells bound to nylon mesh," *European Journal of Immunology* 5: 624–627, 1975.

Schlossman and Hudson, "Specific Purification of Lymphocyte Populations on a Digestible Immunoabsorbent," *Journal of Immunology* 110(1): 313–315, 1973.

Wigzell and Andersson, "Cell Separation on Antigen–Coated Columns: Elimination of High Rate Antibody–Forming Cells and Immunological Memory Cells," *Journal of Experimental Medicine* 129(1):23–36, 1969.

Edelman and Rutishauser, "Specific Fractionation and Manipulation of Cells with Chemically Derivatized Fibers and Surfaces," *Methods in Enzymology* 34: 195–225, 1974.

Norton and Williams, "Cell Sorting by Immunoaffinity Chromatography," *Biotechniques* 1: 96–100, 1983.

Goding, James W., "Affinity Chromatography Using Monoclonal Antibodies," *Monoclonal Antibodies: Principles and Practice*,2nd ed., Academic Press, Sydney, 1986, pp. 219–223.

*Cell Affinity Chromatography: Principles & Methods*, Pharmacia Fine Chemicals, 1980, pp. 8–18.

Klaus (ed.), *Lymphocytes: A Practical Approach*, IRL Press, Oxford, 1987, pp. 1,26.

Gorin, "Cryopreservation and Storage of Stem Cells," in Areman et al., *Bone Marrow and Stem Cell Processing: A Manual of Current Techniques*, F.A. Davis Co., Philadelphia, 1992 pp. 292–308.

Rose et al., (eds.), *Manual of Clinical Laboratory Immunology*, 3rd ed., American Society for Microbiology, Wash., D.C., 1986, p. 843.

Henry et al., "Nylon Wool," in Mishell et al., *Selected Methods in Cellular Immunology*, W.H. Freeman & Co., San Francisco, 1980, pp. 182–185.

5,695,989

APPARATUS AND METHOD FOR SEPARATING PARTICLES USING A PLIABLE VESSEL

CROSS-REFERENCES TO RELATED APPLICATIONS

This application is a file wrapper continuation of U.S. patent application No. 08/116,899, filed Sep. 3, 1993, now abandoned, which is a continuation of U.S. patent application Ser. No. 07/957,408, filed Nov. 18, 1992, now abandoned, which is a continuation of U.S. patent application Ser. No. 07/599,796, filed Oct. 18, 1990, now abandoned.

TECHNICAL FIELD

The present invention relates to a method and apparatus for selectively isolating and/or separating target particles from a mixture of target particles and non-target particles.

BACKGROUND OF THE INVENTION

Various immunoselection methods exist for separating a particular cell subpopulation, or target cells, from a mixture of cells. Many such methods are discussed in detail in the background portion of PCT Publication No. WO 91/16116, now abandoned, which is incorporated by reference herein. For instance, such methods include gross separation with centrifuges, separation by killing of unwanted cells, separation with fluorescence-activated cell sorters, separation by directly or indirectly binding cells to a ligand immobilized on a physical support, separation using panning techniques, separation by column immunoabsorption, and separation using magnetic immunobeads. The problems associated with each of these methods is discussed in detail in co-pending application Ser. No. 07/513,543.

As an improvement to these methods, co-pending application Ser. No. 07/513,543 discloses a device and method for separating target particles bound indirectly to a first member from a mixture of target particles and non-target particles. The device includes a column into which the mixture is to be introduced, a bed of porous binding material disposed within the column having a second member which is capable of binding to the first member, the interstitial spaces of the material being sized to allow the particles to flow through the bed, and a means located within the column for agitating the porous material such that the bound particles are released from the porous material. Various means for agitating the porous material are disclosed in the co-pending application, including magnetic impellers, magnetic beads, weights, magnetic weights, pipettes and buoyant floats. Additional techniques for separating a target cell from a binding material include chemical and enzymatic treatment.

The various agitating techniques discussed above require a relatively large diameter column for accommodating an agitation device such as an impeller or magnetic beads. Therefore, these techniques are not necessarily advantageous for the separation of small volumes of cells in which a column having a diameter as small as 1/16 of an inch is preferred. Furthermore, each of these agitating mechanisms requires the manufacture of additional components resulting in additional expense.

SUMMARY OF THE INVENTION

The present invention resides in a method and device for separating target particles from a mixture of target and non-target particles. The device includes a pliable vessel having an inlet through which fluid may enter and an outlet through which fluid may exit, at least a portion of the vessel being pliable; and a bed of binding material disposed within the vessel, the binding material being capable of binding the target particles such that the target particles become immobilized thereon, wherein the bed includes interstitial spaces of a size sufficient to allow the particles to flow through the bed when the mixture is introduced into the vessel, the pliable portion of the vessel being adapted to cause relative movement of the binding material upon the application of a suitable force, the relative movement being sufficient to dislodge the target particles from the binding material. In a preferred embodiment of the invention, the vessel is in the shape of a column having a separate inlet and outlet respectively disposed at opposite ends of the column, although other shapes could be used.

Depending on the type of binding material, the device may further include a screen for retaining the binding material in the vessel. Further, according to a preferred embodiment of the invention, the target particles may be biological particles, such as cells, which are separated by affinity separation.

Within a related aspect of the invention, a system is provided for separating target particles from a mixture containing target and non-target particles. The system includes a pliable vessel having an inlet through which fluid may enter and an outlet through which fluid may exit, at least a portion of which is pliable; a bed of binding material disposed within the vessel, the binding material being capable of binding the target particles such that the target particles become immobilized thereon, wherein the bed includes interstitial spaces of a size sufficient to allow the particles to flow through the bed when the mixture is introduced into the vessel, the pliable portion of the vessel being adapted to cause relative movement of the binding material upon the application of a suitable force, the relative movement being sufficient to dislodge the target particles from the binding material; and deforming means for deforming the pliable portion of the vessel in such a manner as to cause relative movement in the binding material, the target particles being dislodged from the binding material by deforming the pliable portion of the vessel.

While the above device and system have been described for separating target particles from a mixture containing target and non-target particles, the device and system may also be used to separate target particles from a solution containing only target particles.

As noted above, the present invention also provides a method for separating target particles from a mixture of target and non-target particle. The method includes passing the mixture through the device described above; removing the non-target particles from the vessel; deforming the pliable portion of the vessel so as to cause relative movement in the binding material such that the target particles become dislodged from the binding material; and recovering the target particles from the vessel. As noted above, depending on the type of binding material utilized, the method may further include maintaining the position of the binding material in the vessel by providing a screen which supports the binding material and which allows the mixture to pass therethrough. In a preferred embodiment, the target particles are biological particles, such as cells, which may be separated by affinity separation techniques.

Similarly, another method is provided for separating target particles from solution. The method includes passing the solution through a device as described above such that the solution containing the target particles comes into contact with the binding material such that the target particles become bound to the binding material; removing the unbound portion of the solution from the vessel; deforming the pliable portion of the vessel so as to cause relative movement in the binding material such that the target particles become dislodged from the binding material; and recovering the target particles from the vessel.

These and other aspects will become evident upon reference to the following detailed description of the attached drawings.

DETAILED DESCRIPTION OF THE INVENTION

Figure 1:
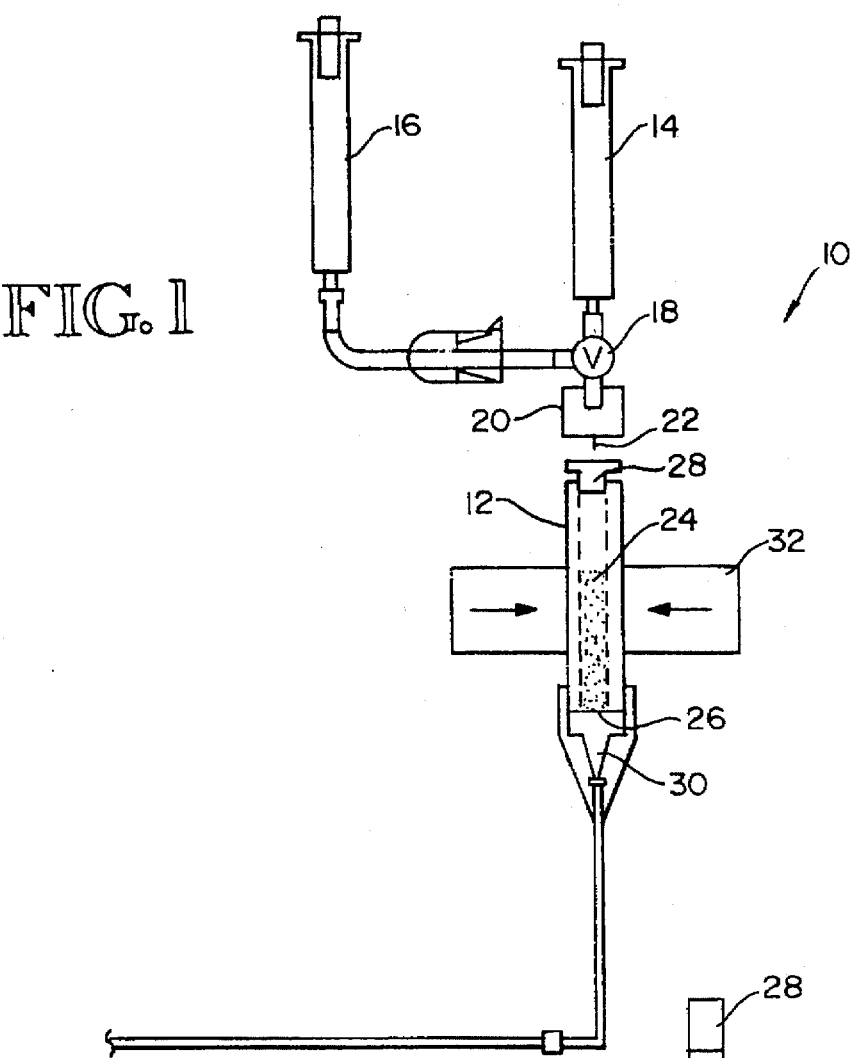
FIG. 1 is a front elevational view of an apparatus including a representative device of the present invention.

As noted above, the present invention is directed to an apparatus and method for separating target particles from a mixture of target particles and non-target particles. FIG. 1 illustrates a particle separating apparatus including a representative device of the present invention. Referring thereto, the system 10 includes a pliable vessel, specifically a column 12, a mixture syringe 14 communicating with the pliable column for introducing a mixture containing target particles and non-target particles, and a wash syringe 16 containing a wash fluid for flushing the column. As is described in detail below, while in a preferred embodiment of the invention the entire column is pliable, only a portion of the column need be pliable. A three-way valve 18 is provided for controlling the introduction of the mixture and the wash into the column. Disposed below the valve 18 is a shrouded needle 20 for injecting either the mixture or the wash into the column through a needle port 22 covering the top portion thereof.

Figure 2:
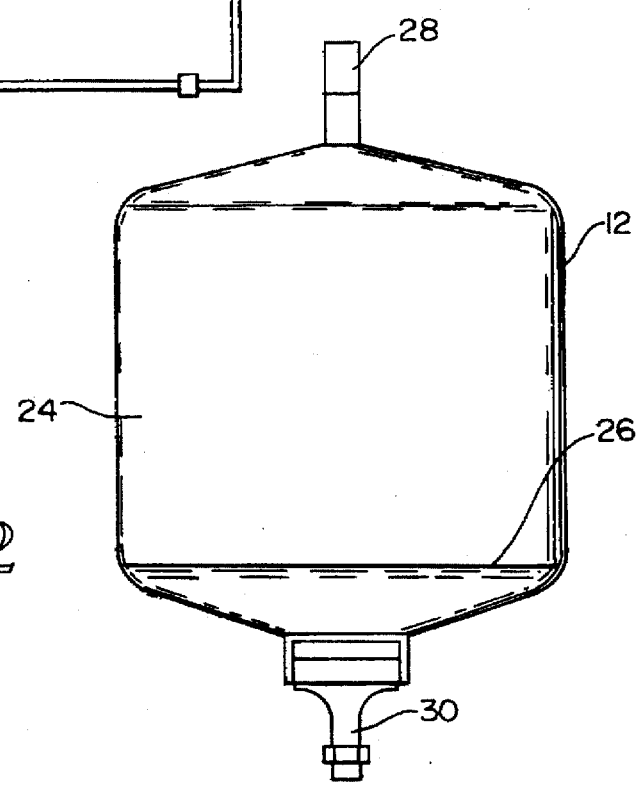
FIG. 2 is a front elevational view of a representative device of the present invention.

Referring to FIG. 2, the column 12 has a bed of binding material 24 disposed therein and a screen 26 positioned below the binding material for maintaining the position of the binding material in the column. The column has an inlet 28 through which the mixture and wash is introduced and an outlet 30 through which components of the mixture flow from the column. Alternatively, the column may have a single opening for introducing the mixture into the column and for removing the mixture from the column.

The pliable vessel may be formed in a number of convenient shapes. As noted above, according to a preferred embodiment of the invention, the vessel is a column. Alternative shapes include a tube, bottle or bag. However, it is understood that the invention is not to be limited to these shapes. Moreover, while in a preferred embodiment the entire vessel is pliable, it is understood that only a portion of the column need be pliable. In a preferred embodiment of the invention, a vessel or portion thereof is pliable if an applied force of less than 30 lb. causes displacement of more than 10% of the binding material without causing the vessel to rupture or crack. As described in detail below, the purpose of the pliable portion is to permit the user to repeatedly apply a force to the pliable potation of the column as necessary to cause relative movement of the binding material. Thus, for example, the column may be manufactured out of rigid material with the exception of a portion of the walls adjacent the binding material. Examples of pliable materials include plasticised polyvinyl chloride, polyethylene, polypropylene, polyurethane, silicon rubber, PVDC (Saran®), SCLAIR®, Surlyn® (packaging film), C-FLEX®, polyester, rubber, some fluoro polymers, or metal films such as aluminum or copper films, for example.

The binding material 24 is designed to bind to the target particles when the mixture containing the target particles and non-target particles is introduced into the column, and to allow the non-target particles to pass therethrough. Thus, the bed of binding material must include interstitial spaces or pores of a size which is sufficient to allow the non-target particles to pass through the bed when the mixture of target and non-target particles is introduced into the column. The specific type of binding material utilized depends on the target particles intended to be separated. The binding material must, to some degree, bind the target particles so that the target particles will become immobilized upon the binding material by forces other than gravitational forces.

As explained in detail below, the mixture of target particles and non-target particles is introduced into the column from the mixture syringe 14. Since the binding material binds the target particles, the target particles become bound thereto while the non-target particles pass through the binding material, thus separating the target particles from the non-target particles. Thereafter, the target particles are dislodged from the binding material, preferably, by repeatedly deforming the pliable portion of the column such that there is relative movement of the binding material. The pliable portion of the column can be deformed in a variety of ways, for instance, by simply squeezing the pliable portion with one's hand or with mechanical means schematically illustrated in FIG. 1. Accordingly, the unique pliable column design permits the binding material to be agitated without the need for an internal agitation device.

The target particles may include organic, inorganic, solid or liquid particles, preferably having a diameter of greater than 0.1 um. However, according to a preferred embodiment of the invention, one group of target particles includes biological particles, such as viruses, bacteria, fungi, parasites and cells. Cells include, among other types of cells, classes of human cells, such as endothelial cells, tumor cells, pancreatic islet cells, macrophages, monocytes, NK cells, B lymphocytes, T lymphocytes, and hematopoietic stem cells.

It will be evident that target cells may be separated from non-target cells using a number of techniques, including affinity separation, where the binding material utilizes a ligand or antibody that specifically binds to the target cells. The target cells may be separated in a "direct" method by passing them through the column, at least a portion of which is pliable as described above, containing a bed of binding material, preferably low nonspecific binding porous material, having a ligand capable of specifically binding to the target particles immobilized on the surface thereof. Alternatively, the target cells may be bound directly or indirectly to a first member and passed over a bed of binding material (such as low nonspecific binding porous material) which has a second member immobilized on the surface thereof. The second member is capable of binding to the first member with an affinity of greater than about $10^8$ $M^{-1}$, and thus is capable of indirectly immobilizing the target cells onto the binding material. A variety of materials may function as a support for the ligand or antibody, including, among others, porous hollow fibers (Amicon Corporation, Danvers, Mass.), beads (Polysciences, Warrington, Pa.), magnetic beads (Robbins Scientific, Mountain View, Calif.), meshes (Becton Dickinson, Mountain View, Calif.), screens and solid fibers (Edelman et al., U.S. Pat. No. 3,843,324; and Kuroda et al., U.S. Pat. No. 4,416,777). It should be noted that the screen 26 is not necessary when the binding material consists of beads (for example, when the beads are larger than the size of the outlet) or fibers which are capable of maintaining their position without a retaining device.

As noted above, the second member allows the indirect binding of the target cells to the binding material through a one-step method involving a ligand first member. The second member may be selected from many first member/second member binding pairs, including, among others, biotin-avidin, biotin-streptavidin, biocytin-streptavidin, methotrexate-dihydrofolate reductase, 5-flourouracil-thimydylate synthetase, riboflavin-riboflavin binding protein (see Becuar and Palmer, "The Binding of Flavin Derivatives to the Riboflavin Binding Protein of Egg White," *J. Biol. Chem.* 257(10):5607–17, 1982), antibody-protein A, and antibody-protein G. Either member of the above described binding pairs may function as the second member, with the complementary member functioning as the first member. Thus, either member may be attached to the binding material, with the complementary member being attached to the ligand.

After the mixture containing the target cells and the non-target cells has been introduced into the column containing the binding material, the non-target cells pass through the material while the target cells become bound to the binding material, as explained above. To dislodge the target cells from the binding material, the pliable portion of the column is, preferably, repeatedly deformed by applying inward pressure to the extent necessary to cause relative movement in the binding material. The degree of deformation is gradually increased until the affinity material is visibly moved. The level of agitation may then be fine-tuned. For example, a lower force may be utilized to remove only nonspecifically bound particles followed by a greater force to remove the most tightly bound particles. Finally, after the target cell have become dislodged from the binding material, the target cells are washed from the column by wash fluid from the wash syringe 16.

As noted above, it has been discovered that by agitating the binding material in this manner, the cell viability is significantly improved as compared to agitation by pipetting. Moreover, since no internal agitation device is required in the column, the diameter of the column can be relatively small (1/16 of an inch), which may be advantageous when separating small volumes of target cells.

While a particularly preferred embodiment of the invention has been described with reference to a ligand or antibody specifically binding to target cells, it is of course understood that the present invention is not limited to the use of such a high affinity binding material for separating target particles, such as cells, from non-target particles. Rather, any binding material which serves to sufficiently bind a target particle, biological or non-biological, could be used. Additionally, the device and method can be used to separate target particles from a solution. For instance, a hydrophobic chromatography resin may be used as the binding material for capturing lipid vesicles in an aqueous solution to thereby separate the lipid vesicles from the aqueous solution. Thereafter, the lipid vesicles can be dislodged from the resin by squeezing the pliable portion of the column so as to cause the resin to experience relative movement. The lipid vesicles can then be eluted by flushing the wash fluid from the wash syringe 16 through the column so as to cause the lipid vesicles to exit the column.

The following examples are being offered by way of illustration and not by way of limitation.

EXAMPLES

EXAMPLE 1

ISOLATION OF STEM CELLS

A. PREPARING THE BUFFY COAT CELLS

A sample of bone marrow is centrifuged at 240 g for 15 minutes. The plasma is removed, and the buffy coat cells are aspirated and centrifuged once more at 240 g for 15 minutes in order to remove residual red blood cells. The buffy coat cells are washed twice with PBS by centrifugation at 280 g for 10 minutes. The cells are then resuspended to a final concentration of $1 \times 10^8$ white cells/ml in PBS plus 1% BSA.

B. INCUBATION OF BUFFY COAT CELLS WITH ANTIBODY

The suspension of buffy coat cells is incubated with a final concentration of 20 µg/ml biotinylated anti-CD34 antibody (Quantum Biosystems, Waterbeach Cambridge, U.K.) at room temperature for 5 minutes. The antibody-cell mixture is then washed twice with PBS plus 1% BSA by centrifugation at 280 g for 10 minutes. The cells are then resuspended at a concentration of $1 \times 10^8$ white cells/ml in PBS plus 5% BSA.

C. CARBOXYLATION OF A POLYACRYLAMIDE GEL

Seventeen grams of dry Biogel P-60™ (50–100 mesh (wet), coarse beads) (BIORAD, Catalog No. 150, 1630, Richmond, Calif.) are added to 1.5 L of 10.5M $Na_2CO_3$. The pH is adjusted to 10.5 with NaOH and carefully stirred with a mixer (RZR1, Carfamo, Wiarton, Ontario, Canada) so as not to damage the beads for approximately 20 to 30 minutes. The mixture is then placed in a 60° C. water bath. After the mixture reaches a temperature of 60° C., it is incubated for an additional 2 hours (at 60° C.) with occasional stirring. The mixture is then removed from the water bath, and placed in an ice bath to bring the mixture temperature down to room temperature.

The beads are washed several times with distilled or deionized water, followed by several washings with PBS using a coarse glass filter connected to a vacuum. The carboxylated gel may be stored in PBS at 4° C., and is stable for up to one year if sterilized or stored with a preservative.

D. AVIDIN CONJUGATING THE CARBOXYLATED BIOGEL

PBS is first removed from a measured amount of carboxylated Biogel by filtering with a coarse glass filter connected to a vacuum. The gel is then equilibrated in distilled or deionized water for 15 to 30 minutes. Equilibration in water causes an expansion of the gel to a volume of about 4 times its previously measured amount. The gel is resuspended in 10 ml of distilled or deionized water for each ml of gel (as originally measured in PBS).

Thirty mg of 1-ethyl-3-(3-dimethylaminopropyl) carbodiimide (EDC-HCl) (Sigma Chemical Co., Catalog No. E7750, St. Louis, Mo.) is added for each ml of gel as originally measured. The pH is rapidly adjusted to 5.5 by dropwise addition of HCl. Care is taken to maintain the pH at 5.5; pHs of less than 5.0 or greater than 6.0 result in significantly less activation of the Biogel. The mixture is stirred for 5 minutes.

Avidin (International Enzymes, Inc., Fallbrook, Calif.) is dissolved at a concentration of between 10 and 100 mg/ml in deionized water. Next, 1 mg of avidin is rapidly added for each ml of gel (as originally measured in PBS). The mixture is stirred for 1.5 hours. Next, 2M glycine is added to give a final concentration of 0.2M glycine in the mixture, and stirred for an additional 1 hour.

The gel is washed with several volumes of PBS using a coarse glass filter and vacuum, and stored in PBS with 1% benzoic acid at 4° C. The gel is stable for approximately one year.

E. COLUMN PREPARATION

K9/15 columns (Pharmacia LKB Biotechnology Inc., Piscataway, N.J.) are assembled with 80 micron nylon mesh in the endcap. Tubing is fitted to the endcap and threaded through a peristaltic pump (Cole Parmer, Chicago, Ill.) to a collection tube. Avidin-coated Biogel prepared above is added to the column in PBS and settled to a depth of 4 cm. Air bubbles in the gel bed are removed by agitation with a pipette. The gel in the column is washed and equilibrated with PBS+5% BSA. Precolumns are made from K9/15 columns as above except that they are filled with a 1 cm bed of carboxylated P-30 gel and the tubing from the bottom of each precolumn leads into the top of the avidin-Biogel-filled column immediately below. The liquid level in each column is drawn down to the level of the gel.

A pliable vessel, as illustrated in FIG. 2, is fabricated from medical grade PVC film with an 80 micron screen in the PVC endcap. Tubing is connected to the endcap and threaded through a peristaltic pump (Cole Parmer, Chicago, Ill.) to a collection tube. The avidin-coated Biogel, prepared as described above, is added to the column in PBS, and settled to a depth of 4 cm. Air bubbles in the gel bed are removed by squeezing the vessel walls. The gel in the vessel is washed and equilibrated with PBS+5% BSA. A precolumn is made from a K9 column with carboxylated gel as described above, and the precolumn outlet tubing is introduced into the spike port at the top of the vessel.

F. COLUMN OPERATION

The $5 \times 10^8$ bone marrow cells treated above are gently layered onto the top of the carboxylated gel in the precolumn and allowed to flow by gravity into the avidin-coated Biogel column below at about 1 ml/min. The cell mixture is pumped through the avidin-coated Biogel column at 1 ml/min. The precolumn is washed with 1–2 mls of PBS+5% BSA after the cell solution passes through. As the last of the cell solution enters the avidin-coated gel, 2 ml of PBS+5% BSA is gently added to that column to wash residual cells through the bed. Before the last of the PBS+5% BSA level enters the bed, PBS is layered gently on top of the solution, forming an interface. The bed is washed with an additional 8 ml of PBS before adherent cells are recovered. The adherent cells are released from the gel by agitating the gel through a pipette while flowing PBS at about 3 ml/min. through the column.

G. PLIABLE VESSEL OPERATION

Five billion bone marrow cells treated as above are layered onto the gel in the precolumn and pumped through the pliable vessel (FIG. 2) at 3.5 ml/min. The precolumn is washed with 5 ml of PBS+5% BSA, and then the pliable vessel is washed with 150 ml of PBS to remove nonadherent cells. The adherent cells are removed from the vessel by stopping PBS flow to the vessel, then manually squeezing the vessel walls to displace the gel within the vessel a dozen times. PBS flow is resumed to the vessel to wash the released cells from the vessel.

H. RESULTS

The K9 column and pipette agitation gave 89% pure CD34 positive cells but only recovered 45% of the initial number of CD34 positive cells (as determined by FACS staining). The final cell viability, as determined by trypan blue exclusion, was only 80%. The cells purified using the pliable vessels were 92% pure, contained 56% of the initial number of CD34 positive cells, and were 98% viable. The greatly enhanced viability observed from the pliable vessels can be attributed to improved agitation, while the improved yield might also be a result of the different operating conditions, such as flow rate.

EXAMPLE 2

SEPARATION OF SMALL SAMPLE OF CELLS

Effective separation of small numbers of cells requires a very small volume of avidin-coated gel, or the purity of the recovered adherent cells is significantly reduced by the number of cells which bind nonspecifically on the vessel walls or the affinity gel.

A. PREPARATION OF CELLS

Peripheral blood is centrifuged at 280 g for 15 minutes. The plasma is removed and the layer containing white blood cells is aspirated. The white blood cells are resuspended in PBS and centrifuged once more at 280 g for 15 minutes to remove residual red blood cells. The buffy coat cells are resuspended in PBS+0.1% HSA at a concentration of $10^8$/ml and incubated with biotinylated anti-Ia antibody (1 µg/ml) for 5 minutes at room temperature. (Described in "Immunoselection" application.)

B. PREPARATION OF GEL AND SEPARATION VESSEL

The carboxylated and avidin-coated gels are prepared as described in parts C and D of Example 1. A pliable vessel is constructed of PVC tubing and medical infusion components as illustrated in FIG. 1. The tubing containing the avidin-coated gel (number 12 in FIG. 1) has an internal diameter of 3.5 mm. Because of the small diameter, there is not room for inclusion of a weight or magnet for agitating the gel to remove cells, nor is there room for a pipette tip. Furthermore, the bubbles frequently generated when agitating gel to remove cells would completely block the tubing bore. The pliable vessel was prepared for use as described in Example 1 above.

A second pliable vessel, as illustrated in FIG. 1, is fabricated from PVC tubing and infusion set components. The vessel is filled with avidin-coated Biogel to a depth of 4 cm in PBS, and the outlet tubing is threaded through a peristaltic pump. The gel is equilibrated with PBS+5% BSA and the tubing is primed to remove air. The wash reservoir is filled with 10 ml of PBS. Carboxylated gel (½ ml) is settled in the sample reservoir to form the precolumn.

C. SEPARATION VESSEL OPERATION

Fifteen million buffy-coat peripheral blood cells prepared in part A above are added to the sample reservoir. The cells are pumped through the device at 0.1 ml/min and the reservoir is washed with 0.2 ml of PBS+1% HSA. Before the last of the wash is pumped from the sample reservoir, the three-way valve is turned to stop flow from the sample reservoir and to allow the PBS from the wash reservoir to flow through the device to remove nonspecific cells. After the vessel has been washed, the adherent cells are removed by manually squeezing the tubing holding the avidin-coated gel a dozen times while flowing the PBS solution to wash the released cells into a collection tube.

D. RESULTS

Three million Ia positive cells were bound and recovered from the device with a purity of 89%, as determined by FACS analysis. This represented a yield of 70% of the Ia positive cells in the original blood sample. The viability as measured by trypan blue was unchanged by the separation operation.

As can be seen by the foregoing, the device of the present invention provides a simple means for separating target particles from solution or from a mixture of target particles and non-target particles. It will be appreciated that, although specific embodiments of the invention have been described herein for the purpose of illustration, various modifications may be made without departing from the spirit and scope of the invention. Accordingly, the invention is not to be limited except as by the appended claims.

What is claimed is:

1. A device for separating target particles from a mixture containing target particles and non-target particles, comprising:

a vessel having an inlet through which fluid may enter and an outlet through which fluid may exit, at least a portion of said vessel being pliable; and a bed of binding material disposed within said vessel, said binding material having a ligand on the surface thereof which is capable of specifically binding said target particles either directly or indirectly such that said target particles become immobilized thereon wherein the bed includes interstitial spaces of a size sufficient to allow the mixture to flow through the bed when the mixture is introduced into said vessel, the pliable portion of said vessel being adapted such that upon application of less than 30 lb. force against said pliable portion, more than 10% of said binding material is displaced without rupturing said pliable portion, thereby dislodging the target particles from the binding material.

2. The device of claim 1 wherein said inlet and outlet are a single opening in said vessel.

3. The device of claim 1 wherein the entire vessel is pliable.

4. The device of claim 1, further comprising means for retaining said binding material in said vessel.

5. The device of claim 1 wherein said binding material is porous.

6. The device of claim 1 wherein said binding material is capable of specifically binding biological particles.

7. The device of claim 1 wherein said binding material is capable of separating said target particles from said mixture by affinity separation.

8. A system for separating target particles from a mixture containing target particles and non-target particles, comprising:

a vessel having an inlet through which fluid may enter and an outlet through which fluid may exit, at least a portion of said vessel being pliable;

a bed of binding material disposed within said vessel, said binding material having a ligand on the surface thereof which is capable of specifically binding said target particles either directly or indirectly such that said target particles become immobilized thereon wherein the bed includes interstitial spaces of a size sufficient to allow the mixture to flow through the bed when the mixture is introduced into said vessel, said pliable portion of said vessel being adapted such that upon application of less than 30 lb. force against said pliable portion, more than 10% of said binding material is displaced without rupturing said pliable portion, thereby dislodging the target particles from the binding material; and deforming means for deforming said pliable portion in such a manner as to cause relative movement of said binding material, said target particles being dislodged from said binding material by deforming said pliable portion of said vessel.

9. The system of claim 8 wherein said inlet and outlet are a single opening in said vessel.

10. The system of claim 8 wherein the entire vessel is pliable.

11. The system of claim 8, further comprising means for retaining said binding material in said vessel.

12. The system of claim 8 wherein said binding material is porous.

13. The system of claim 8 wherein said binding material is capable of specifically binding biological particles.

14. The system of claim 8 wherein said binding material is capable of separating said target particles from said mixture by affinity separation.

15. A device for separating target particles from a solution, comprising:

a vessel having an inlet through which fluid may enter and an outlet through which fluid may exit, at least a portion of said vessel being pliable; and a bed of binding material disposed within said vessel, said binding material having a ligand on the surface thereof which is capable of specifically binding said target particles either directly or indirectly such that said target particles become immobilized thereon wherein the bed includes interstitial spaces of a size sufficient to allow the solution containing particles to flow through the bed when the solution is introduced into said vessel, said pliable portion of said vessel being adapted such that upon application of less than 30 lb. force against said pliable portion, more than 10% of said binding material is displaced without rupturing said pliable portion, thereby dislodging the target particles from the binding material.

16. A device for separating target particles from a mixture containing target particles and non-target particles, comprising:

a vessel having an inlet through which fluid may enter and an outlet through which fluid may exit, at least a portion of said vessel being pliable; and a bed of porous binding material disposed within said vessel, said binding material having a ligand on the surface thereof which is capable of specifically binding said target particles either directly or indirectly such that said target particles become immobilized thereon wherein the size of the pores of said porous material is sufficient to allow the mixture to flow through the bed when the mixture is introduced into said vessel, said pliable portion of said vessel being adapted such that upon application of less than 30 lb. force against said pliable portion, more than 10% of said binding material is displaced without rupturing said pliable portion, thereby dislodging the target particles from the binding material.

* * * * *